US 8,247,779 B2

(12) United States Patent
Kameshima et al.

(10) Patent No.: US 8,247,779 B2
(45) Date of Patent: Aug. 21, 2012

(54) RADIATION IMAGING APPARATUS, ITS CONTROL METHOD, AND RADIATION IMAGING SYSTEM

(75) Inventors: Toshio Kameshima, Kumagaya (JP); Tadao Endo, Honjo (JP); Tomoyuki Yagi, Honjo (JP); Katsuro Takenaka, Honjo (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 493 days.

(21) Appl. No.: 12/490,926

(22) Filed: Jun. 24, 2009

(65) Prior Publication Data

US 2009/0323897 A1 Dec. 31, 2009

(30) Foreign Application Priority Data

Jun. 27, 2008 (JP) ................................ 2008-169470

(51) Int. Cl.
*G01T 1/24* (2006.01)
(52) U.S. Cl. .................................. 250/370.09
(58) Field of Classification Search ............. 250/370.08, 250/370.09, 370.11, 370.14; 378/98.8, 116
See application file for complete search history.

(56) References Cited

U.S. PATENT DOCUMENTS

| | | | | |
|---|---|---|---|---|
| 5,648,660 A * | 7/1997 | Lee et al. | ............... | 250/370.09 |
| 7,012,260 B2 | 3/2006 | Endo | ............... | 250/370.11 |
| 7,154,099 B2 | 12/2006 | Endo | ............... | 250/370.11 |
| 7,227,926 B2 * | 6/2007 | Kameshima et al. | ........ | 378/98.9 |
| 7,343,000 B2 * | 3/2008 | Kameshima et al. | ........ | 378/98.9 |
| 7,386,089 B2 | 6/2008 | Endo et al. | ........ | 378/5 |
| 7,408,167 B2 | 8/2008 | Kameshima et al. | .... | 250/370.11 |
| 7,470,911 B2 | 12/2008 | Yagi | ........ | 250/370.14 |
| 7,514,690 B2 | 4/2009 | Endo et al. | ........ | 250/370.14 |
| 7,573,041 B2 | 8/2009 | Kameshima et al. | .... | 250/370.09 |
| 7,592,599 B2 | 9/2009 | Kameshima | ........ | 250/370.09 |
| 2005/0173645 A1 * | 8/2005 | Endo | ........ | 250/370.11 |
| 2005/0220270 A1 | 10/2005 | Kameshima et al. | ........ | 378/98.9 |
| 2007/0210258 A1 | 9/2007 | Endo et al. | ........ | 250/370.09 |
| 2009/0001276 A1 | 1/2009 | Yagi et al. | ........ | 250/370.09 |
| 2009/0140155 A1 | 6/2009 | Yagi et al. | ........ | 250/370.09 |
| 2009/0146071 A1 | 6/2009 | Kameshima et al. | .... | 250/370.09 |
| 2009/0166547 A1 | 7/2009 | Endo et al. | ........ | 250/370.14 |
| 2010/0046711 A1 | 2/2010 | Kameshima et al. | ........ | 378/98.8 |

* cited by examiner

*Primary Examiner* — David Porta
*Assistant Examiner* — Marcus Taningco
(74) *Attorney, Agent, or Firm* — Fitzpatrick, Cella, Harper & Scinto

(57) ABSTRACT

A radiation imaging apparatus having high frame rate and picture quality by offset correction has: a sensor array having matrix-shaped pixels each including a converting element and a TFT; a driver for supplying signals to control terminals of the TFTs row by row; a reader for holding a signal in a first or second sampling/holding (S/H) circuit and outputting an image signal; and a controller for controlling the driver and reader. Until the image signal is output after irradiation of the apparatus with pulsating radiation, the TFT of a pixel is driven so as to output a first signal, the TFT of the pixel to which the first signal has been output is driven so as to output a second electric signal, and the reader outputs the image signal of the signal showing a difference between the first and second signals held in the first and second S/H circuits.

8 Claims, 8 Drawing Sheets

RADIATION IMAGING APPARATUS, ITS CONTROL METHOD, AND RADIATION IMAGING SYSTEM

BACKGROUND OF THE INVENTION

1. Field of the Invention

The present invention relates to a radiation imaging apparatus, its control method, and a radiation imaging system.

2. Description of the Related Art

In recent years, a flat panel detector having an area sensor array in which an amorphous silicon film formed on an insulating substrate such as glass or the like is used as a material and pixels each of which is constructed by a photoelectric converting element and a thin film transistor (TFT) are two-dimensionally arranged has been applied to a medical X-ray radiographing apparatus or the like.

The X-ray radiographing apparatus using such a flat panel detector and a driving method of such an apparatus have been disclosed in, for example, U.S. Patent Application Publication No. 2005/0220270 or the like. An X-ray radiographing apparatus in which signals are read out by matrix-driving flat panel detectors using amorphous silicon has been disclosed in U.S. Patent Application Publication No. 2005/0220270. In the imaging apparatus using flat panel detectors using amorphous silicon, by applying a driving signal to a gate of a thin film transistor, the thin film transistor is driven and the signal is read out. At this time, in addition to an image lag (afterimage) and untransferred charges of the thin film transistor, an offset that is caused by the driving operation of the thin film transistor is added to the read-out signal. A signal to noise ratio of the signal thus obtained deteriorates, causing a deterioration in picture quality. To prevent the deterioration in picture quality, according to U.S. Patent Application Publication No. 2005/0220270, after radiographing image data of the number corresponding to one image was obtained, offset image data of the number corresponding to one image is obtained, and the offset image data of one image is subtracted from the radiographing image data of one image, thereby making offset correction.

SUMMARY OF THE INVENTION

In an X-ray radiographing apparatus which is used for operations, a medical diagnosis, or the like and can perform fluoroscopic radiographing (fluoroscopy being motion image radiographing), good picture quality, a high frame rate, and instantaneousness of a process are demanded. However, according to U.S. Patent Application Publication No. 2005/0220270, there are the following problems.

First, to obtain the offset-corrected image, time to obtain the image data of two images and time required to execute the subtraction of the image data of two images are necessary. Consequently, a substantial decrease in frame rate occurs, and there is a problem in that in some cases it is difficult to obtain both satisfactory picture quality and satisfactory frame rate. Particularly, in the thin film transistor, since its operating speed is lower than that of a transistor of a crystalline semiconductor by about two to three digits (orders of magnitude), the decrease in frame rate becomes remarkable. In other words, the problem that it is difficult to obtain both satisfactorily high picture quality and satisfactorily high frame rate can be regarded as a problem that is peculiar to imaging apparatus using a thin film transistor as a component element of a pixel.

Since the arithmetic operating process is executed after the radiographing image data and the offset image data were determined, there is a problem in that there are cases where instantaneousness of a display or the like is insufficient.

The present invention is made in consideration of the foregoing problems, and it is an object of the invention to provide a radiation imaging apparatus, its control method, and a radiation imaging system, in which good picture quality is assured by offset correction while assuring a high frame rate.

According to the invention, there is provided a radiation imaging apparatus comprising: a sensor array constructed by arranging, in a matrix form, a plurality of pixels each including a converting element configured to convert radiation into charges and a thin film transistor which has a control terminal and two main terminals and in which one of the two main terminals is connected to the converting element in order to output an electric signal according to the charges; a driving circuit configured to supply signals to the control terminals of the plurality of thin film transistors on a row-unit basis; a reading circuit configured to hold the electric signal read out through the other one of the two main terminals into a first sampling and holding circuit or a second sampling and holding circuit and output an image signal based on the electric signal; and a control unit configured to control the driving circuit and the reading circuit, where, for a period of time until the image signal is output after the apparatus is irradiated with pulse-shaped radiation, the control unit allows the driving circuit to drive the thin film transistor of a predetermined pixel, thereby allowing a first electric signal to be output from the predetermined pixel, allows the driving circuit to drive the thin film transistor of the predetermined pixel in which the first electric signal has been output, thereby allowing a second electric signal to be output from the predetermined pixel, and allows the reading circuit to output the image signal based on an electric signal corresponding to a difference between the first electric signal held in the first sampling and holding circuit and the second electric signal held in the second sampling and holding circuit.

According to the invention, there is also provided a radiation imaging system comprising: the radiation imaging apparatus; and a radiation generating apparatus configured to irradiate the radiation to the radiation imaging apparatus.

According to the invention, there is also provided a control method of a radiation imaging apparatus having a sensor array constructed by arranging, in a matrix form, a plurality of pixels each including a converting element configured to convert radiation into charges and a thin film transistor which has a control terminal and two main terminals and in which one of the two main terminals is connected to the converting element in order to output an electric signal according to the charges, a driving circuit configured to supply signals to the control terminals of the plurality of thin film transistors on a row-unit basis, and a reading circuit configured to hold the electric signal read out through the other one of the two main terminals into a first sampling and holding circuit or a second sampling and holding circuit and output an image signal based on the electric signal, where, for a period of time until the image signal is output after the apparatus is irradiated with pulse-shaped radiation, the control method comprises: a first outputting step of allowing the driving circuit to drive the thin film transistor of a predetermined pixel, thereby allowing a first electric signal to be output; a second outputting step of allowing the driving circuit to drive the thin film transistor of the predetermined pixel in which the first electric signal has been output, thereby allowing a second electric signal to be output; and a third outputting step of allowing the reading circuit to read out the first electric signal and the second electric signal and outputting the image signal based on an electric signal corresponding to a difference between the first electric signal and the second electric signal.

According to the invention, good picture quality can be assured by the offset correction while also assuring the desired high frame rate. Particularly, even in the case where the offset fluctuates, the mentioned good picture quality and high frame rate can be realized.

Further features of the present invention will become apparent from the following description of exemplary embodiments with reference to the attached drawings.

DESCRIPTION OF THE PREFERRED EMBODIMENTS

Preferred embodiments of the present invention will now be described in detail in accordance with the accompanying drawings.

First Embodiment

In an imaging apparatus using a thin film transistor (TFT) as a component element of a pixel, the present inventors have found out a construction of a radiation imaging apparatus suitable for a fluoroscopic radiographing (fluoroscopy) or the like and a driving method in consideration of a feature of a fluctuation of an offset. Specifically speaking, among phenomena that may be regarded as an "offset" as that term used herein, there are an image lag (afterimage), untransferred charges of the thin film transistor, an offset that is caused by the driving operation of the thin film transistor, and the like. A construction of the first embodiment of the invention will be described further in detail hereinbelow with reference to the drawings.

Figure 1:
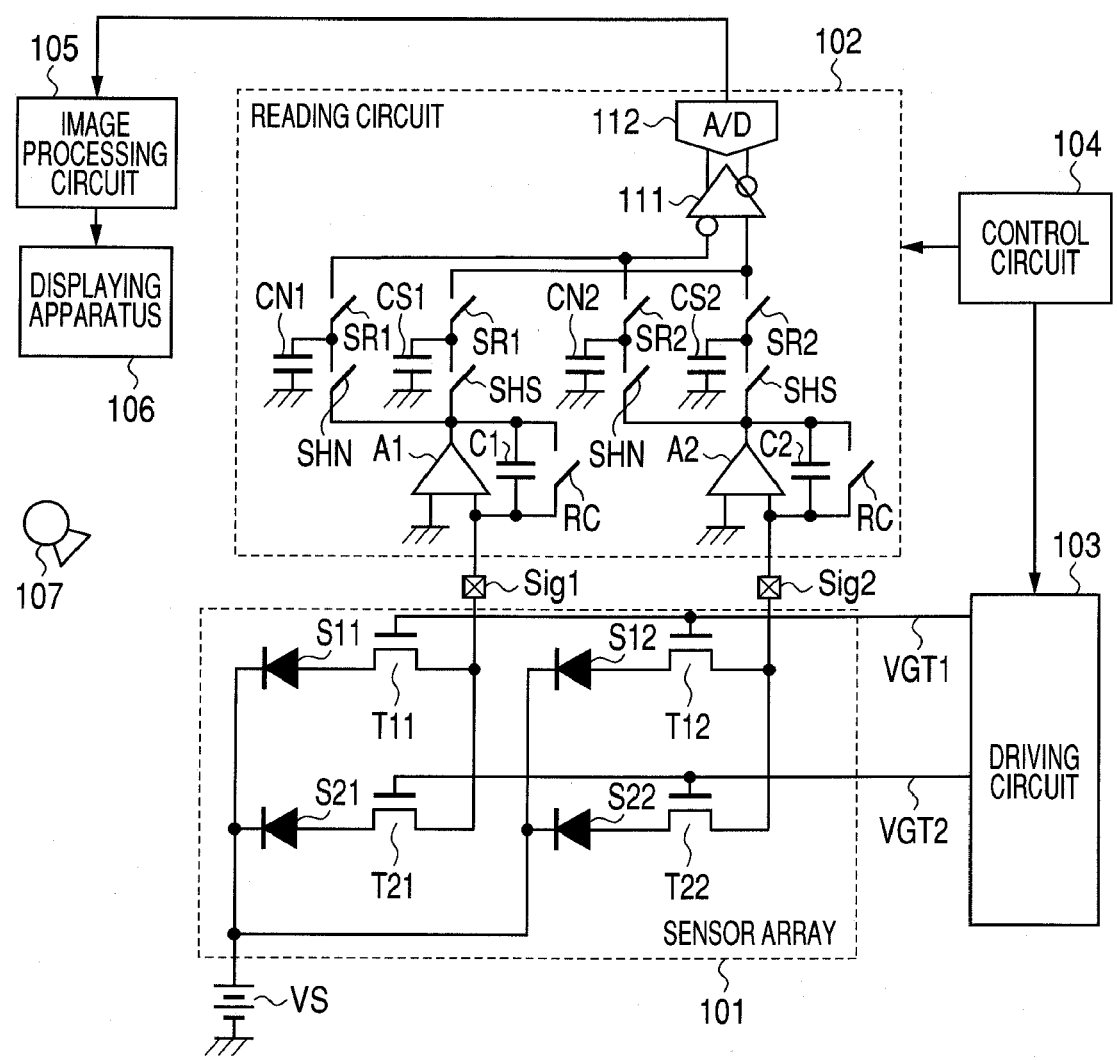
FIG. 1 is a constructional diagram of a radiation imaging apparatus according to the first embodiment of the invention.

FIG. 1 is a constructional diagram of the radiation imaging apparatus according to the first embodiment of the invention.

Figure 2:
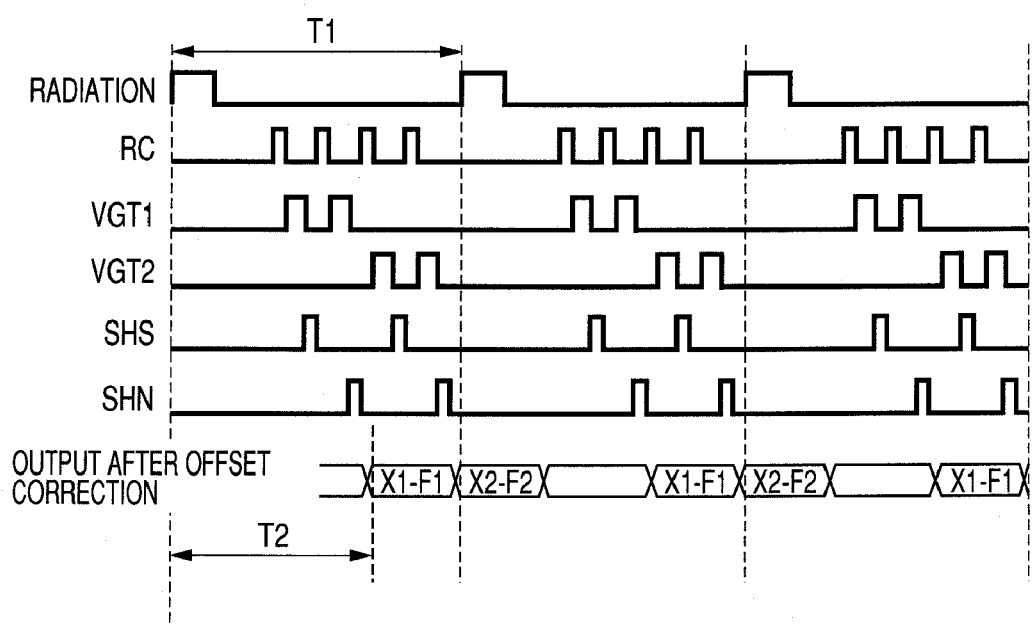
FIG. 2 is a timing chart for the radiation imaging apparatus according to the first embodiment of the invention.
Figure 3:
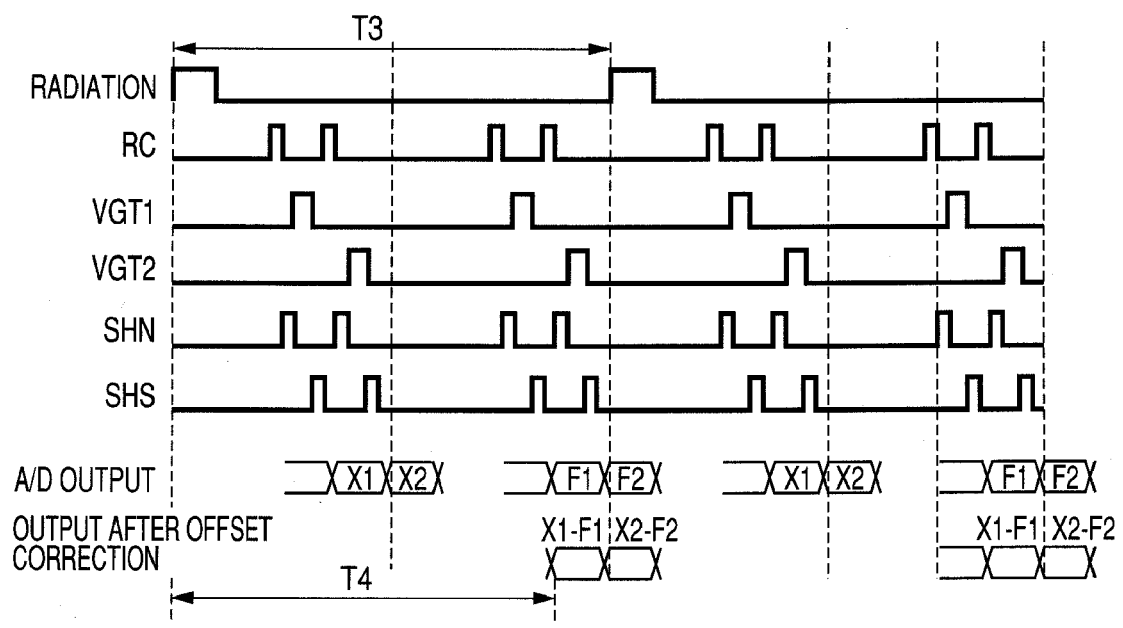
FIG. 3 is a timing chart for the radiation imaging apparatus according to the first embodiment of the invention.
Figure 4:
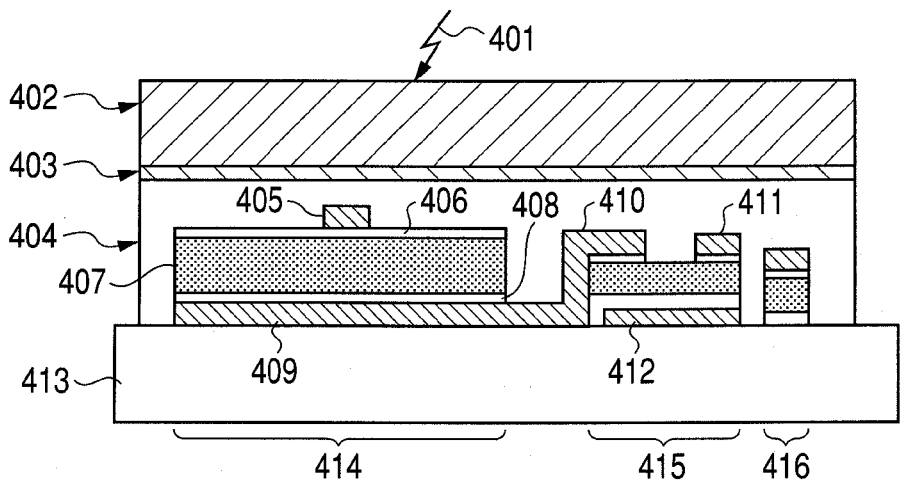
FIG. 4 is a cross sectional view of a pixel of a flat panel detector according to the first embodiment of the invention.

FIG. 2 is a timing chart for describing a control method of the radiation imaging apparatus according to the first embodiment of the invention. FIG. 3 is a timing chart for describing another control method of the radiation imaging apparatus according to the first embodiment of the invention. FIG. 4 is a cross-sectional view of a pixel of the radiation imaging apparatus according to the first embodiment of the invention.

In FIG. 1, PIN-type photodiodes S11 to S22 are photoelectric converting elements each for converting light into charges. Anodes of the photodiodes S11 to S22 are respectively connected to drains or sources of thin film transistors T11 to T22 and cathodes are respectively connected to a bias power source VS. FIG. 4 is a cross-sectional view of a pixel in a sensor array 101. The converting element in FIG. 4 has a phosphor layer 402 and a photodiode 414 and converts radiation (for example, X-rays) 401 into charges. The phosphor layer 402 is a wavelength converter for converting the radiation 401 into light. The photodiode 414 corresponds to each of the photodiodes S11 to S22 and converts the light into charges. Details of FIG. 4 will be described hereinafter. The bias power source VS applies a bias voltage to one electrode of the photoelectric converting element through a bias wiring.

A radiation generating apparatus 107 in FIG. 1 irradiates pulse-shaped radiation (X-rays) 401 onto the sensor array 101 through an object to be radiographed at a radiation pulse interval T1 in FIG. 2. Thus, the converting element in FIG. 4 converts the radiation 401 into electric charges.

The thin film transistors T11 to T22 output electric signals corresponding to the charges converted by the converting elements (including the photodiodes S11 to S22). Gates (control terminals) of the thin film transistors T11 to T22 are electrically connected to a driving circuit 103. The converting elements are electrically connected to the drains or sources (one of two main terminals of each TFT) of the thin film transistors T11 to T22. A signal wiring Sig1 is electrically connected to the sources or drains (the other one of the two main terminals of each TFT) of the thin film transistors T11 and T21. A signal wiring Sig2 is electrically connected to the sources or drains of the thin film transistors T12 and T22.

In the sensor array 101, a plurality of pixels is arranged in a matrix form. One pixel includes one converting element (including one of the photodiodes S11 to S22) and one of the thin film transistors T11 to T22.

The driving circuit 103 is constructed by, for example, a shift register. The driving circuit 103 supplies driving signals to the gates of a plurality of thin film transistors T11 to T22 in the row direction through gate wirings VGT1 and VGT2, thereby sequentially driving the thin film transistors T11 to T22 on a row-unit basis (row by row). The gates of the thin film transistors T11 and T12 are connected to the gate wiring VGT1. The gates of the thin film transistors T21 and T22 are connected to the gate wiring VGT2. The driving circuit 103 supplies driving signals to the gate wirings VGT1 and VGT2. As illustrated in FIG. 2, when the gate wiring VGT1 is set to the high level, the thin film transistors T11 and T12 are turned on. Thus, the charges converted by the photodiodes S11 and S12 are output to the signal wirings Sig1 and Sig2 through the sources or drains of the thin film transistors T11 and T12, respectively. When the gate wiring VGT2 is set to the high level, the thin film transistors T21 and T22 are turned on. Thus, the charges converted by the photodiodes S21 and S22 are output to the signal wirings Sig1 and Sig2 through the sources or drains of the thin film transistors T21 and T22, respectively. Thus, the sensor array 101 sequentially outputs the electric signals (signals of one pixel) to the signal wirings Sig1 and Sig2 in parallel on a row unit basis.

Subsequently, a construction of a reading circuit 102 will be described. The reading circuit 102 reads out the electric signals through the signal wirings Sig1 and Sig2 connected in common to the sources or drains of the plurality of thin film transistors T11 to T22 in the column direction and outputs an image signal. The image signal is an electric signal of one frame.

The reading circuit 102 has at least operational amplifiers A1 and A2, a first sampling and holding circuit (for the radiation signal), and a second sampling and holding circuit (for the offset signal) every signal wirings Sig1 and Sig2.

One input terminal of the operational amplifier A1 is connected to the signal wiring Sig1 and the other input terminal is connected to a reference potential node (for example, ground potential node). A feedback capacitor C1 and a reset switch RC are connected in parallel between the one input terminal and an output terminal of the operational amplifier A1. One input terminal of the operational amplifier A2 is connected to the signal wiring Sig2 and the other input terminal is connected to the reference potential node (for example, ground potential node). A feedback capacitor C2 and the reset switch RC are connected in parallel between the one input terminal and an output terminal of the operational amplifier A2. When a control signal of the reset switch RC in FIG. 2 is set to the high level, the reset switch RC is turned on and the feedback capacitors C1 and C2 and the signal wirings Sig1 and Sig2 are reset.

The first sampling and holding circuit has a set of capacitors CS1 and CS2 and a switch SHS. The second sampling and holding circuit has a set of capacitors CN1 and CN2 and a switch SHN. When a control signal of the switch SHS is set to the high level after the irradiation of the radiation in FIG. 2, the switch SHS is turned on. An output signal of the operational amplifier A1 is accumulated as a radiation signal X1 into the capacitor CS1. An output signal of the operational amplifier A2 is accumulated as a radiation signal X2 into the capacitor CS2. After that, when a control signal of the switch SHN is set to the high level, the switch SHN is turned on. The output signal of the operational amplifier A1 is accumulated as an offset signal F1 into the capacitor CN1. The output signal of the operational amplifier A2 is accumulated as an offset signal F2 into the capacitor CN2.

In FIG. 2, the radiation signal X1 is a signal of the pixels of the first row at the time when the radiation has been irradiated. The offset signal F1 is a signal of the pixels of the first row at the time when the radiation is not irradiated. The radiation signal X2 is a signal of the pixels of the second row at the time when the radiation has been irradiated. The offset signal F2 is a signal of the pixels of the second row at the time when the radiation is not irradiated.

The reading circuit 102 further has first multiplexers SR1 and SR2 connected to the first sampling and holding circuit and second multiplexers SR1 and SR2 connected to the second sampling and holding circuit.

The reading circuit 102 further has a differential amplifier 111 and an A/D converter 112. One input terminal of the differential amplifier 111 is connected to the first multiplexer SR1 or SR2 for the radiation signal and the other input terminal is connected to the second multiplexer SR1 or SR2 for the offset signal.

When a switch of the multiplexer SR1 is turned on, the differential amplifier 111 subtracts the offset signal F1 or F2 in the capacitor CN1 or CN2 from the radiation signal X1 or X2 in the capacitor CS1 or CS2 and outputs a signal indicative of a difference between them as a signal after the offset correction. When a switch of the multiplexer SR2 is turned on, the differential amplifier 111 subtracts the offset signal F1 or F2 in the capacitor CN2 from the radiation signal X1 or X2 in the capacitor CS2 and outputs a signal indicative of a difference between them as an image signal after the offset correction. By sequentially turning on the multiplexer SR1 and SR2, the differential amplifier 111 can time-sequentially output the image signals on a pixel unit basis.

The first sampling and holding circuit, the second sampling and holding circuit, and the differential amplifier 111 serve as a CDS circuit (correlation duplex sampling circuit).

The A/D converter 112 converts an analog output signal of the differential amplifier 111 into a digital signal and outputs the digital signal to an image processing circuit 105. The image processing circuit 105 executes an image process to the image signal and outputs the processed signal to a displaying apparatus 106. The displaying apparatus 106 displays a motion image based on the image signal.

A control circuit 104 controls the driving circuit 103 and the reading circuit 102. The control circuit 104 executes the following processes for a period of time until the image signal is output from the reading circuit 102 after the pulse-shaped radiation is irradiated onto the apparatus. That is, the control circuit 104 drives the thin film transistors T11 to T22 so as to generate a first electric signal serving as a radiation signal X1 or X2. After that, the control circuit 104 drives the thin film transistors T11 to T22 again and drives the sensor array 101 so as to generate a second electric signal serving as an offset signal F1 or F2. That is, an image lag component that is caused by past irradiation history of the converting elements and offset components of the thin film transistors T11 to T22 are output as a second electric signal.

The reading circuit 102 reads out the first electric signal and the second electric signal for a period of time until the image signal is output from the reading circuit 102 after the pulse-shaped radiation is irradiated onto the apparatus and outputs the image signal based on the electric signal indicative of the difference between the first and second electric signals.

That is, the radiation imaging apparatus can output the image signal obtained by subtracting the offset signal F1 or F2 from the radiation signal X1 or X2 for a period of time during which the image signal of one frame is output. In this embodiment, since the differential process between the image signals which are output from the reading circuit 102 as disclosed in foregoing U.S. Patent Application Publication No. 2005/0220270 is unnecessary, a time (processing delay) T2 from the irradiation of the radiation onto the apparatus to completion of the differential process is shorter than that in U.S. Patent Application Publication No. 2005/0220270 in which the differential process is executed between the image signals. Consequently, a displaying delay to the displaying apparatus 106 can be also shortened.

A control method of the radiation imaging apparatus will be described further in detail with reference to FIGS. 1 and 2. First, under preset conditions, the radiation is irradiated from the radiation generating apparatus 107. The radiation which has penetrated the object and includes object information enters the sensor array 101. Subsequently, the reset switches RC provided for the operational amplifiers A1 and A2 of the signal wirings Sig1 and Sig2 are turned on by the high-level control signal of the reset switch RC. Thus, the feedback capacitors C1 and C2 of the operational amplifiers A1 and A2 connected to the signal wirings Sig1 and Sig2 and the signal wirings Sig1 and Sig2 are reset. Subsequently, a transfer pulse is applied to the gate wiring VGT1 and the thin film transistors T11 and T12 connected to the gate wiring VGT1 are turned on. The charges generated in the photodiodes S11 and S12 are transferred to the reading circuit 102 through the signal wirings Sig1 and Sig2. The transferred charges are converted into voltages by the operational amplifiers A1 and A2 connected to the signal wirings Sig1 and Sig2. Subsequently, the high-level control signal is supplied to the switch SHS of the first sampling and holding circuit. The voltage outputs from the operational amplifiers A1 and A2 are sampled and accumulated as a radiation signal X1 into the capacitors CS1 and CS2.

The radiation signal X1 includes the offset component in addition to the object information. That is, the radiation signal X1 includes the image lag that is caused by defects in the amorphous silicon film, the untransferred charges of the thin film transistors T11 to T22, the offset that is caused by the driving operation of the thin film transistors T11 to T22, or the like.

Subsequently, the radiation is not irradiated (that is, it is not generated or at least does not strike the subject or the imaging apparatus), the feedback capacitors C1 and C2 and the signal wirings Sig1 and Sig2 are again reset by the high-level control signal of the reset switch RC. The transfer pulse is applied again to the gate wiring VGT1 and the thin film transistors T11 and T12 are turned on. The charges in the photodiodes S11 and S12 are transferred to the reading circuit 102 through the signal wirings Sig1 and Sig2. The transferred charges are now sampled by the high-level control signal of the switch SHN of the second sampling and holding circuit and accumulated as an offset signal F1 into the capacitors CN1 and CN2.

The offset signal F1 mainly includes the image lag that is caused by the defects in the amorphous silicon film, the untransferred charges of the thin film transistors T11 to T22, the offset that is caused by the driving operation of the thin film transistors T11 to T22, or the like. In this manner, with respect to the pixels connected to the gate wiring VGT1, the radiation signal X1 including the object information and the offset information is sampled by the switch SHS and the offset signal F1 including the offset information is sampled by the switch SHN.

In the embodiment, the reading circuit 102 has the differential amplifier 111. The differential amplifier 111 obtains a difference between the radiation signal X1 and the offset signal F1 which have been sampled by the switches SHS and SHN. The A/D converter 112 converts the analog difference signal into the digital signal and outputs the offset-corrected digital signal.

Subsequently, the feedback capacitors C1 and C2 and the signal wirings Sig1 and Sig2 are reset again by the high-level control signal of the reset switch RC. The transfer pulse is applied again to the gate wiring VGT2 and the thin film transistors T21 and T22 are turned on. The charges formed by the photodiodes S21 and S22 are transferred to the reading circuit 102 through the signal wirings Sig1 and Sig2. The transferred charges are sampled by the high-level control signal of the switch SHS of the first sampling and holding circuit and accumulated as a radiation signal X2 in the capacitors CS1 and CS2.

Subsequently, the feedback capacitors C1 and C2 and the signal wirings Sig1 and Sig2 are again reset by the high-level control signal of the reset switch RC. The transfer pulse is applied again to the gate wiring VGT2 and the thin film transistors T21 and T22 are turned on. The charges in the photodiodes S21 and S22 are transferred to the reading circuit 102 through the signal wirings Sig1 and Sig2. The transferred charges are sampled by the high-level control signal of the switch SHN of the second sampling and holding circuit and accumulated as an offset signal F2 in the capacitors CN1 and CN2.

The differential amplifier 111 obtains a difference between the radiation signal X2 and the offset signal F2 which have been sampled by the switches SHS and SHN. The A/D converter 112 converts the analog difference signal into the digital signal and outputs the offset-corrected digital signal.

By repetitively executing substantially the same operation as that mentioned above for all rows, the signals of the whole sensor array 101 can be read out.

A reciprocal number of the radiation pulse interval T1 illustrated in FIG. 2 is now defined as a "radiation frame rate", and the time T2 from the start of the radiation pulse to the start of the offset correcting process is defined as a "processing delay". Naturally, it will be understood that the embodiment is superior to that shown in U.S. Patent Application Publication No. 2005/0220270 from the viewpoints of the radiation frame rate and the processing delay.

According to the present embodiment, therefore, the good picture quality, meaning that the offset component has effectively been corrected, and the improvement of the radiation frame rate and the processing delay can be accomplished.

Although not specifically illustrated in FIG. 1, it is more desirable that the control circuit 104 can control the radiation generating apparatus 107, image processing circuit 105, and displaying apparatus 106.

For example, with respect to the information sampled by the switch SHS and the information sampled by the switch SHN, accumulating times in the photodiodes S11 to S22 differ. There is a case where this fact affects the picture quality. In such a case, it is desirable from the viewpoint of improving the picture quality that the image processing circuit 105 executes an arithmetic operating process based on a difference of the accumulating times between them.

FIG. 3 illustrates another example of the control method of the radiation imaging apparatus according to the present embodiment. It is more desirable that the control circuit 104 can make control illustrated in FIG. 3 in addition to the control described in FIG. 2. The control method of FIG. 3 will be described hereinbelow.

First, the radiation pulse is irradiated, the resetting operation is executed by the reset switch RC, and noise signals are accumulated into the capacitors CN1 and CN2 by the switch SHN. After that, the thin film transistors T11 and T12 are turned on by the pulse of the gate wiring VGT1, thereby allowing the charges in the photodiodes S11 and S12 to be output to the signal wirings Sig1 and Sig2. After that, the radiation signals are accumulated in the capacitors CS1 and CS2 by the switch SHS. The differential amplifier 111 subtracts the noise signals in the capacitors CN1 and CN2 from the radiation signals in the capacitors CS1 and CS2 and outputs the radiation signal X1. The A/D converter 112 converts the analog radiation signal X1 into the digital signal.

Subsequently, the resetting operation is executed by the reset switch RC, and the noise signals are accumulated into the capacitors CN1 and CN2 by the switch SHN. After that, the thin film transistors T21 and T22 are turned on by the pulse of the gate wiring VGT2. The charges in the photodiodes S21 and S22 are transferred to the signal wirings Sig1 and Sig2. After that, the radiation signals are accumulated into the capacitors CS1 and CS2 by the switch SHS. The differential amplifier 111 subtracts the noise signals in the capacitors CN1 and CN2 from the radiation signals in the capacitors CS1 and CS2 and outputs the radiation signal X2. The A/D converter 112 converts the analog radiation signal X2 into a digital signal.

Subsequently, the radiation is not irradiated, the resetting operation is executed by the reset switch RC, and the noise signals are accumulated into the capacitors CN1 and CN2 by the switch SHN. After that, the thin film transistors T11 and T12 are turned on by the pulse of the gate wiring VGT1, thereby allowing the charges in the photodiodes S11 and S12 to be output to the signal wirings Sig1 and Sig2. After that, the offset signals are accumulated into the capacitors CS1 and CS2 by the switch SHS. The differential amplifier 111 subtracts the noise signals in the capacitors CN1 and CN2 from the offset signals in the capacitors CS1 and CS2 and outputs the offset signal F1. The A/D converter 112 converts the analog offset signal F1 into the digital signal.

Subsequently, the resetting operation is executed by the reset switch RC and the noise signals are accumulated in the capacitors CN1 and CN2 by the switch SHN. After that, the thin film transistors T21 and T22 are turned on by the pulse of the gate wiring VGT2. The charges in the photodiodes S21 and S22 are transferred to the signal wirings Sig1 and Sig2. After that, the offset signals are accumulated in the capacitors CS1 and CS2 by the switch SHS. The differential amplifier 111 subtracts the noise signals in the capacitors CN1 and CN2 from the offset signals in the capacitors CS1 and CS2 and outputs the offset signal F2. The A/D converter 112 converts the analog offset signal F2 into a digital signal.

The image processing circuit 105 subtracts the offset signal F1 from the radiation signal X1, subtracts the offset signal F2 from the radiation signal X2, and forms the image signal.

A radiation pulse interval T3 in FIG. 3 is longer than the radiation pulse interval T1 in FIG. 2. A processing delay T4 in FIG. 3 is longer than the processing delay T2 in FIG. 2.

In the present control method, after the radiation pulse is irradiated, the gate wirings VGT1 and VGT2 are scanned and the radiation signals X1 and X2 of the pixels of the whole sensor array 101 are read out. Subsequently, the radiation is not irradiated, and meanwhile the gate wirings VGT1 and VGT2 are scanned again, and the offset signals F1 and F2 of the pixels of the whole sensor array 101 are read out.

As mentioned above, it is also possible to construct the apparatus in such a manner that the apparatus has a plurality of pairs of first sampling and holding circuit and second sampling and holding circuit, one pair for each of the signal wirings Sig1 and Sig2, and after the first electric signals of a plurality of rows are continuously read out, the second electric signals of a plurality of rows are continuously read out.

A radiation frame rate (1/T3) and the processing delay T4 in FIG. 3 are smaller than a radiation frame rate (1/T1) and the processing delay T2 in FIG. 2. However, there can be also a case where the control of FIG. 3 is better from the viewpoint of picture quality in dependence on type and operating environment (environmental temperature and the like) of the radiation imaging apparatus.

Therefore, such a construction that the control circuit 104 can properly switch and execute the control of FIG. 2 and the control of FIG. 3 or the control of FIG. 2, and the control of FIG. 3 can be switched by a drive selecting circuit (not shown) adds the special effect that it accommodates differences in type and operating environment of the radiation imaging apparatus.

In FIG. 3, the signal is obtained by the correlation duplex sampling by using the switches SHN and SHS of the sampling and holding circuits. It is more desirable that the reading circuit 102 has the correlation duplex sampling function.

Subsequently, a cross-sectional structure of each pixel of the sensor array 101 in FIG. 1 will be described with reference to FIG. 4. The photodiode 414 corresponds to each of the photodiodes S11 to S22 in FIG. 1. A thin film transistor 415 corresponds to each of the thin film transistors T11 to T22 in FIG. 1. A wiring portion 416 corresponds to each of the signal wirings Sig1 and Sig2 in FIG. 1.

The PIN-type photodiode 414 of each pixel has a construction in which a lower electrode layer 409, an amorphous silicon p layer 408, an amorphous silicon semiconductor layer 407, an amorphous silicon n layer 406, and an upper electrode layer 405 are laminated on a glass substrate 413. The thin film transistor 415 has a construction in which a gate electrode layer (lower electrode) 412, an insulating layer (amorphous silicon nitride film), an amorphous silicon semiconductor layer, an amorphous silicon n layer, a layer of a source electrode (upper electrode) 411, and a layer of a drain electrode (upper electrode) 410 are laminated. The wiring portion 416 indicates each of the signal wirings Sig1 and Sig2 in FIG. 1. Although not illustrated, in each pixel, the wiring portion 416 is connected to the source electrode 411 of the thin film transistor 415. A protecting layer 404 such as an amorphous silicon nitride film or the like having high transmittance against the visible light is provided on the photodiode 414, thin film transistor 415, and wiring portion 416 formed as films on the glass substrate 413 and covers the whole layer. Although the glass substrate 413 is used in the embodiment, the invention is not limited to the glass substrate but can use an arbitrary substrate so long as it has the insulative surface.

In order to apply the invention to the medical radiation imaging system for performing fluoroscopic radiographing (fluoroscopy, or motion image radiographing), the phosphor layer 402 for converting the radiation (X-rays) 401 into visible light is formed over the protecting layer 404, from which it is spaced by an adhesive layer 403. A gadolinium system, cesium iodide, or the like can be used for the phosphor layer 402. The photodiode 414 is a photoelectric converting element for converting the light into electric charges. Therefore, the converting element including the phosphor layer 402 and the photodiode 414 can convert the radiation 401 into charges.

The photoelectric converting element in the sensor array 101 is not limited to the PIN-type photodiode 414 of amorphous silicon. The photoelectric converting element may be an MIS-type photoelectric converting element or an element made of amorphous selenium, gallium arsenide, gallium phosphide, lead iodide, mercury iodide, CdTe, CdZnTe, or the like adapted to directly convert radiation (X-rays) into electric charges.

Further, the material of the thin film transistor 415 is not limited to amorphous silicon, but a thin film transistor made of one of polysilicon and an organic material may be used.

Second Embodiment

Figure 5:
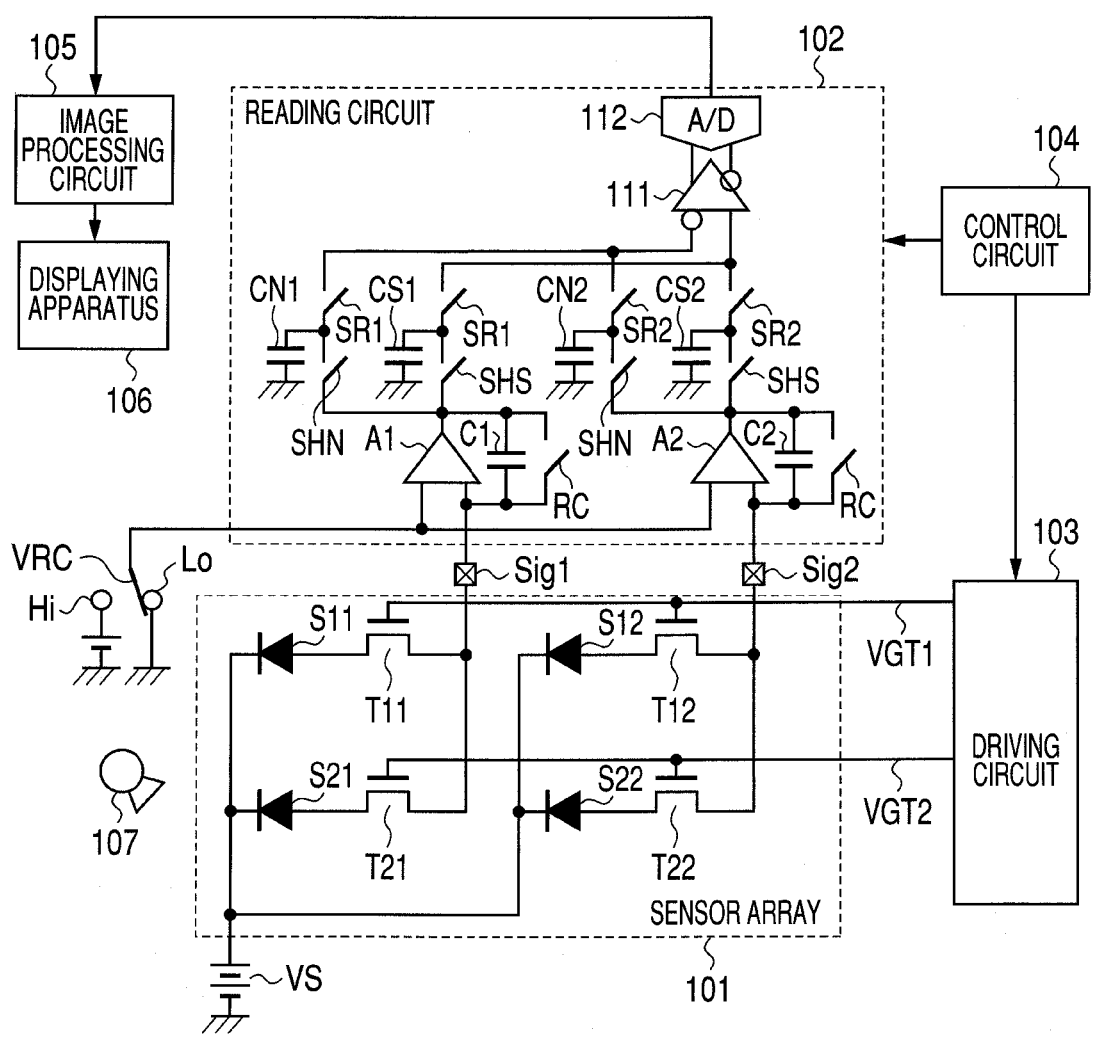
FIG. 5 is a constructional diagram of a radiation imaging apparatus according to the second embodiment of the invention.
Figure 6:
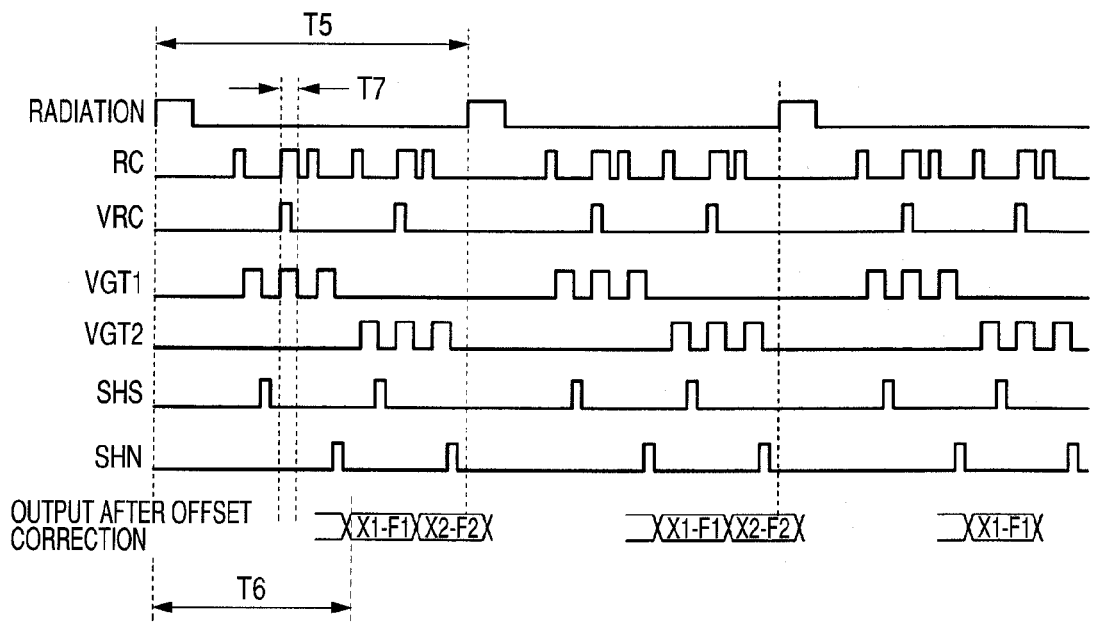
FIG. 6 is a timing chart for the radiation imaging apparatus according to the second embodiment of the invention.
Figure 7:
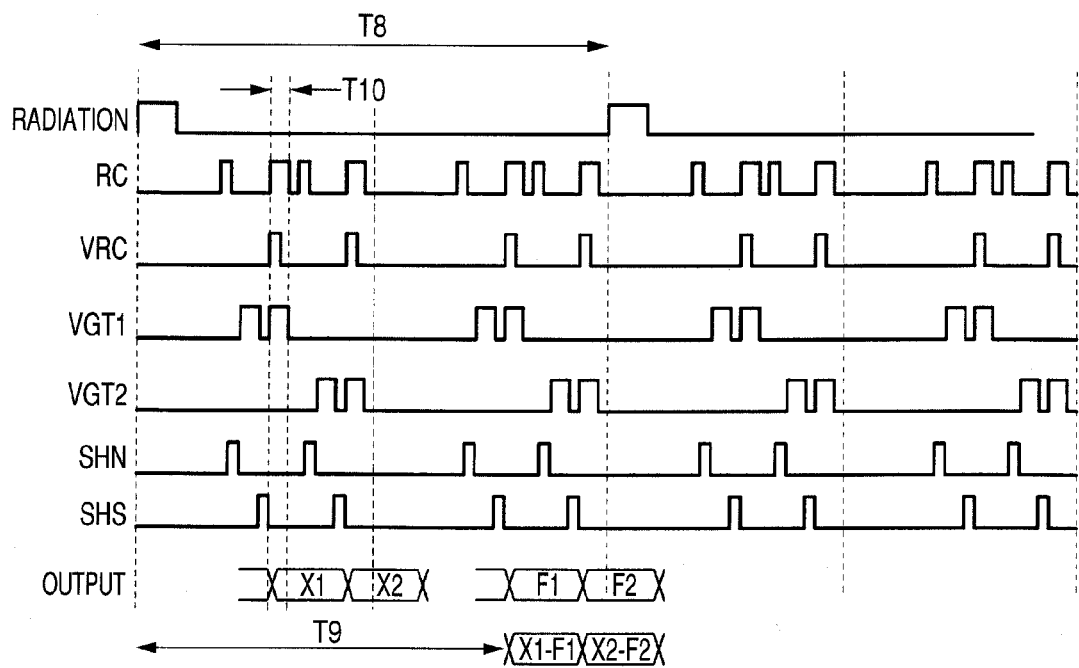
FIG. 7 is a timing chart for the radiation imaging apparatus according to the second embodiment of the invention.

FIG. 5 is a constructional diagram of a radiation imaging apparatus according to the second embodiment of the invention. FIGS. 6 and 7 are timing charts illustrating a control method for the radiation imaging apparatus according to the second embodiment of the invention. FIG. 6 corresponds to FIG. 2 in the first embodiment. FIG. 7 corresponds to FIG. 3 in the first embodiment.

A point in which the second embodiment differs from the first embodiment will be described hereinbelow. In FIG. 5, the control circuit 104 can control a reference potential of the operational amplifiers A1 and A2 in the reading circuit 102 by means of a switch VRC. The other input terminal of each of the operational amplifiers A1 and A2 can be connected to a high-level node Hi or a low-level node Lo by the switch VRC.

In FIG. 6, a reinitialization period (refresh period) T7 for reinitializing the converting elements is added between the sampling and holding timing of the radiation signal X1 or X2 by the first sampling and holding circuit and the output timing of the offset signal F1 or F2, as compared with FIG. 2. A radiation pulse interval T5 and a processing delay T6 are illustrated. The reinitialization period T7 is provided after the pulse control signal of the switch SHS for the radiation signal X1. In the reinitialization period T7, the high-level control signal is input to the reset switch RC, the high-level control signal is input to the switch VRC, and the gate wiring VGT1 is set to the high level. When the control signal is set to the high level, the switch VRC connects the high-level node Hi to the input terminals of the operational amplifiers A1 and A2. When the control signal is set to the low level, the switch VRC connects the low-level node Lo to the input terminals of the operational amplifiers A1 and A2. By the reinitialization period T7, the converting elements (photodiodes S11 and S12) of the first row are reinitialized.

Similarly, a reinitialization period is provided after the pulse control signal of the switch SHS for the radiation signal X2. In the reinitialization period, the high-level control signal is input to the reset switch RC, the high-level control signal is input to the switch VRC, and the gate wiring VGT2 is set to the high level. By this reinitialization period, the converting elements (photodiodes S21 and S22) of the second row are reinitialized.

In FIG. 7, a reinitialization period (refresh period) T10 for reinitializing the converting elements is added to FIG. 3. A radiation pulse interval T8 and a displaying delay T9 are illustrated. The reinitialization period T10 is provided after the pulse control signal of the switch SHS. In the reinitialization period T10, in a manner similar to the reinitialization period T7 in FIG. 6, the high-level control signal is input to the reset switch RC, the high-level control signal is input to the switch VRC, and the gate wiring VGT1 or VGT2 is set to the high level. Thus, the converting elements (photodiodes S11 to S22) can be reinitialized.

The reinitialization periods T7 and T10 correspond to the operation for allowing the converting elements to approach an initial state. Generally, the switch VRC is connected to the low-level node Lo. The switch VRC is connected to the high-level node Hi for the reinitialization periods T7 and T10. In the reinitialization periods T7 and T10, in the case of the PIN type photodiodes S11 to S22, by decreasing the bias between the two electrodes, a depletion layer width is reduced, the charges in the converting elements are emitted, and the converting elements can be made to approach the initial state.

According to the embodiment, in addition to effects similar to those in the first embodiment, the image lag component that is caused by the operations of the thin film transistors T11 to T22 in the reinitialization periods T7 and T10 can be also eliminated. According to the present embodiment, the substantial frame rate can be improved as compared with the form in which the whole area of the sensor array 101 is reinitialized in a "lump". The control circuit 104 may be constructed in such a manner that the control method of FIG. 6 and the control method of FIG. 7 can be properly switched.

Third Embodiment

Figure 8:
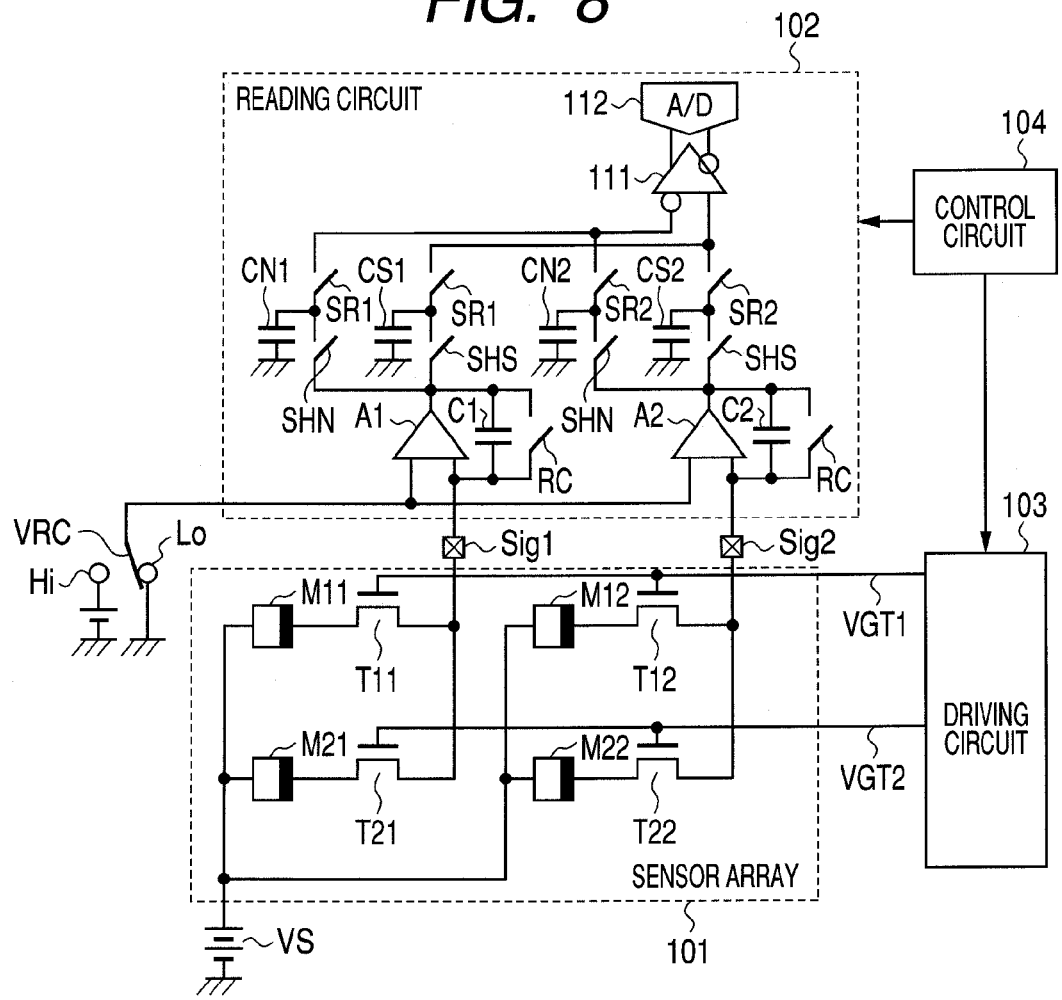
FIG. 8 is a constructional diagram of a radiation imaging apparatus according to the third embodiment of the invention.

FIG. 8 is a constructional diagram of a radiation imaging apparatus according to the third embodiment of the invention. A point in which the third embodiment differs from the second embodiment will be described hereinbelow. As converting elements, MIS-type photoelectric converting elements M11 to M22 are provided in place of the PIN-type photodiodes S11 to S22 in FIG. 5.

Figure 9:
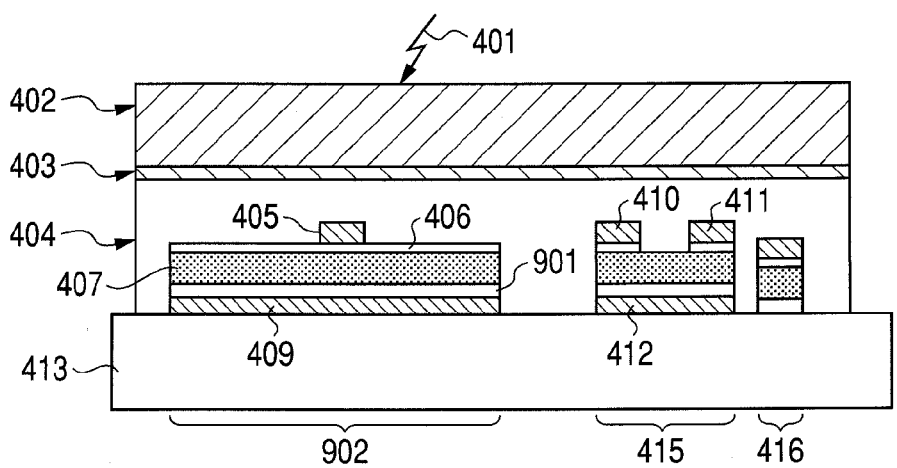
FIG. 9 is a cross-sectional view of a pixel of a flat panel detector according to the third embodiment of the invention.

FIG. 9 is a cross-sectional view of a pixel of the sensor array 101 according to the third embodiment. An MIS-type photoelectric converting element 902 corresponds to each of the MIS-type photoelectric converting elements M11 to M22 in FIG. 8. The MIS-type photoelectric converting element 902 of each pixel has a construction in which the lower electrode layer 409, an insulating layer (amorphous silicon nitride film) 901, the amorphous silicon semiconductor layer 407, the amorphous silicon n layer 406, and the upper electrode layer 405 are laminated on the glass substrate 413. The thin film transistor 415 has a construction in which the gate electrode layer (lower electrode) 412, the insulating layer (amorphous silicon nitride film), the amorphous silicon semiconductor layer, the amorphous silicon n layer, the layer (upper electrode) of the source electrode 411, and the layer (upper electrode) of the drain electrode 410 are laminated.

In order to apply the invention to the medical radiation imaging system for performing fluoroscopic radiographing or the like, the phosphor layer 402 for converting radiation 401 into visible light is formed over the protecting layer 404, from which it is spaced by the adhesive layer 403. The gadolinium system, cesium iodide, or the like can be used for the phosphor layer 402.

It has been known by the examination by the present inventors that in the MIS-type photoelectric converting elements M11 to M22, the offset containing the image lag is caused by the reinitializing operation in the reinitialization periods T7 and T10 in FIGS. 6 and 7. Therefore, according to this embodiment, in addition to the effects similar to those in the first embodiment, the offset can be also eliminated.

As mentioned above, the MIS-type photoelectric converting element 902 has a structure in which the first electrode layer 409, the insulating layer 901, the intrinsic semiconductor layer 407, the impurity semiconductor layer 406, and the second electrode layer 405 are sequentially laminated from the bottom. At the time of the photoelectric conversion, there is applied to the MIS-type photoelectric converting element 902 a bias voltage which applies such an electric field that in a generated electron-hole pair, the electron is pulled out to the second electrode layer 405 side and the hole is accumulated in an interface of the intrinsic semiconductor layer 407 and the insulating layer 901. At the time of the reinitialization, there is applied to the MIS-type photoelectric converting element 902 a bias voltage which applies such an electric field that the hole accumulated in the interface of the intrinsic semiconductor layer 407 and the insulating layer 901 is moved to the second electrode layer 405 side connected to the bias power source VS and is eliminated.

In a manner similar to the second embodiment, the operation for allowing the converting elements to approach the initial state is executed in the reinitialization periods T7 and T10. Generally, the switch VRC is connected to the low-level node Lo. The switch VRC is connected to the high-level node Hi for the reinitialization periods T7 and T10. In the case of the MIS-type photoelectric converting element 902, the hole accumulated in the interface of the intrinsic semiconductor layer 407 and the insulating layer 901 of the photoelectric converting element 902 is moved to the second electrode layer 405 side connected to the bias power source VS and is eliminated, so that the converting elements can be allowed to approach the initial state. Thus, in the present embodiment, the offset components which are caused by the driving operations of the thin film transistors T11 to T22 upon reinitialization can be also eliminated. According to this embodiment, the substantial frame rate can be improved as compared with the form in which the whole area of the sensor array 101 is reinitialized in a "lump".

Fourth Embodiment

Figure 10:
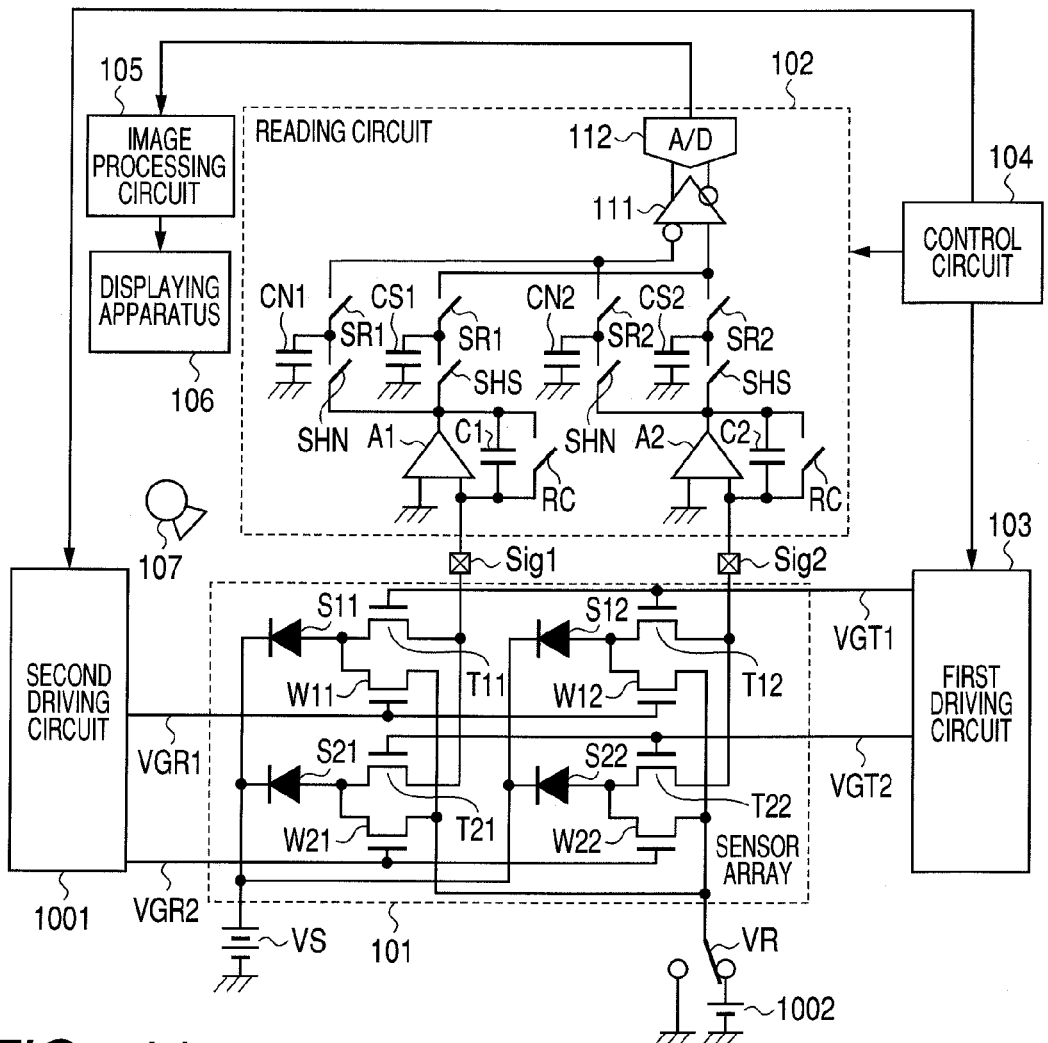
FIG. 10 is a constructional diagram of a radiation imaging apparatus according to the fourth embodiment of the invention.
Figure 11:
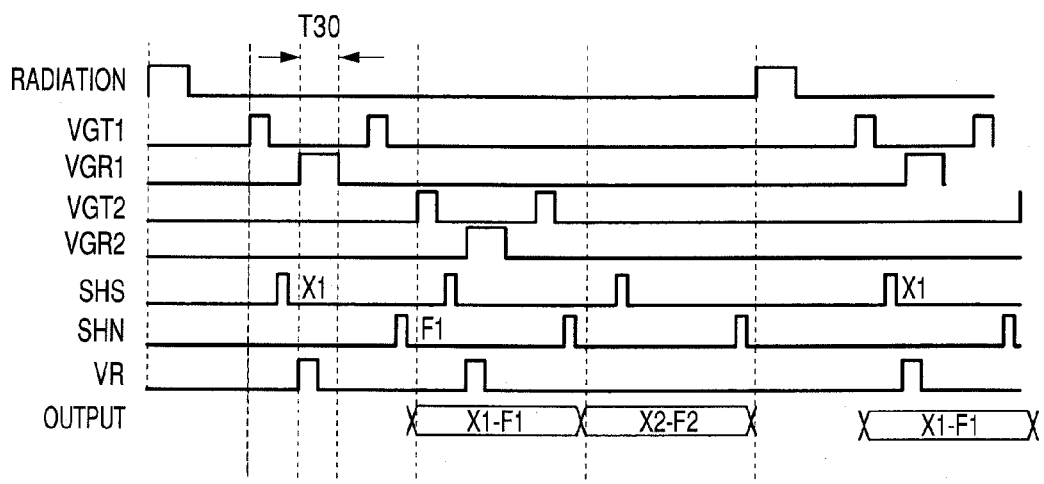
FIG. 11 is a timing chart for the radiation imaging apparatus according to the fourth embodiment of the invention.

FIG. 10 is a constructional diagram of a radiation imaging apparatus according to the fourth embodiment of the invention. FIG. 11 is a timing chart showing a control method for the radiation imaging apparatus according to the fourth embodiment of the invention.

A point in which the fourth embodiment differs from the first embodiment will be described hereinbelow. Each pixel in the sensor array 101 further has thin film transistors W11 to W22 for reinitialization. Gates of the thin film transistors W11 and W12 for reinitialization are connected to a gate wiring VGR1. Gates of the thin film transistors W21 and W22 for reinitialization are connected to a gate wiring VGR2. Drains or sources of the thin film transistors W11 to W12 are connected to a bias power source 1002 or the reference potential node (ground potential node) through a switch VR. That is, an electrode having two kinds of electric potentials is connected in common to one electrode of each of the thin film transistors W11 to W22 for reinitialization. Sources or drains of the thin film transistors W11 to W22 for reinitialization are connected to anodes of the photodiodes S11 to S22, respectively. In order to drive the thin film transistors W11 to W22 for reinitialization, a second driving circuit 1001 applies voltages to the gate wirings VGR1 and VGR2 according to control of the control circuit 104. The first driving circuit 103 corresponds to the driving circuit 103 in FIG. 1.

A reinitialization period T30 is provided between the high-level control signal of the switch SHS for the radiation signals X1 and X2 and the high level of the gate wirings VGT1 and VGT2 for the offset signal F1 or F2. In the reinitialization period T30, the gate wiring VGR1 or VGR2 is set to the high level and the control signal of the switch VR is set to the high level. When the control signal is set to the high level, the switch VR is connected to the bias power source 1002. When the control signal is set to the low level, the switch VR is connected to the reference potential node. In the reinitialization period T30, the thin film transistors W11 to W22 for reinitialization are driven for a period of time between the sampling and holding timing of the radiation signal X1 or X2 by the first sampling and holding circuit and the output timing of the second electric signal, thereby reinitializing the converting elements. In this embodiment, the image lag components which are caused by the driving operations of the thin film transistors W11 to W22 for reinitialization also can be eliminated.

As described above, in the reinitialization period T30 between the sampling by the switch SHS and the sampling by the switch SHN, the thin film transistors W11 to W22 for reinitialization are turned on and the PIN type photodiodes S11 to S22 can be reinitialized. It has been known by the examination by the present inventors that the offset containing the image lag is caused when the thin film transistors W11 to W22 for reinitialization are turned on. In the present embodiment, in addition to the effects similar to those in the first embodiment, such an offset also can be eliminated.

Fifth Embodiment

Figure 12:
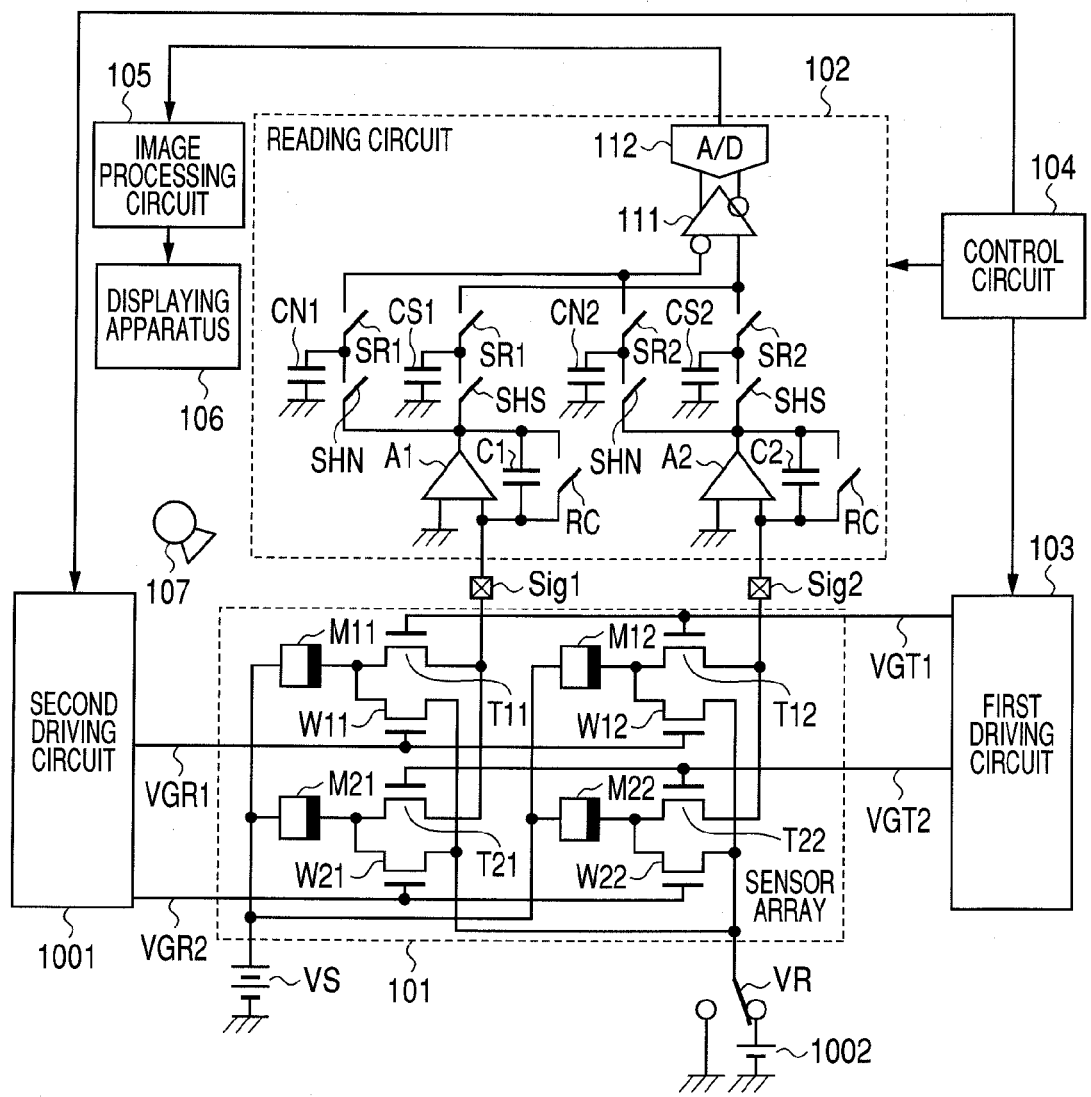
FIG. 12 is a constructional diagram of a radiation imaging apparatus according to the fifth embodiment of the invention.

FIG. 12 is a constructional diagram of a radiation imaging apparatus according to the fifth embodiment of the invention. A point in which the fifth embodiment differs from the fourth embodiment will be described hereinbelow. As converting elements, the MIS-type photoelectric converting elements M11 to M22 are provided in place of the PIN-type photodiodes S11 to S22 in FIG. 10. The structure and operation of the MIS-type photoelectric converting elements M11 to M22 are substantially the same as those in the third embodiment. The fifth embodiment is a combination of the third and fourth embodiments and effects similar to those in the third and fourth embodiments are obtained.

Each pixel has the MIS-type photoelectric converting elements M11 to M22, the thin film transistors T11 to T22 for charge transfer, and the thin film transistors W11 to W22 for reinitialization. As illustrated in FIG. 11, in the reinitialization period T30 between the sampling by the switch SHS and the sampling by the switch SHN, the thin film transistors W11 to W22 for reinitialization are turned on and the MIS type photoelectric converting elements M11 to M22 are reinitialized.

When the thin film transistors W11 to W22 for reinitialization are turned on, the offset containing the image lag is caused. It has been found by the examination by the present inventors that the offset caused here in the case of the MIS-type photoelectric converting elements M11 to M22 is more significant than that in the case of the PIN-type photodiodes S11 to S22. In this embodiment, in addition to the effects similar to those in the first embodiment, this offset also can be eliminated.

Sixth Embodiment

Figure 13A:
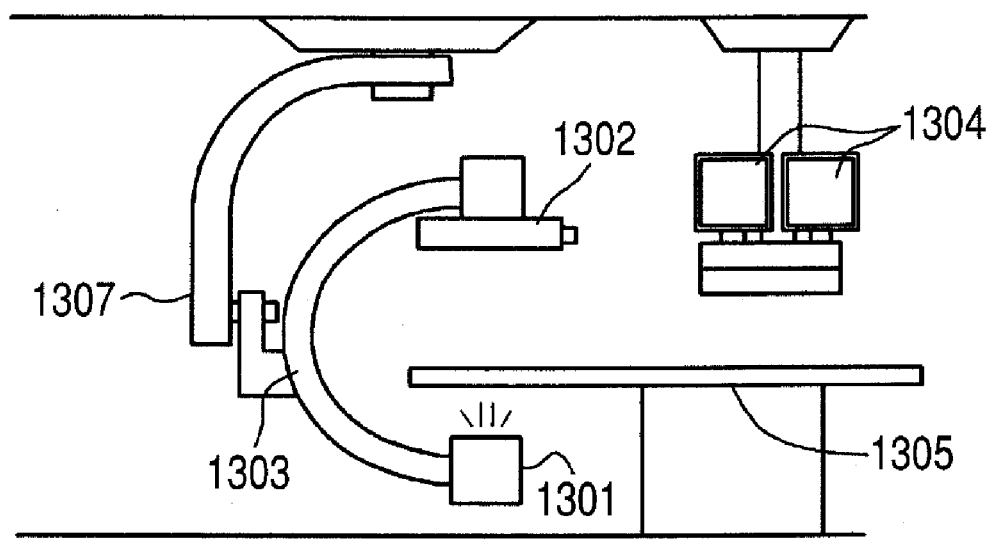
FIGS. 13A and 13B are constructional diagrams of radiation imaging systems according to the sixth embodiment of the invention.
Figure 13B:
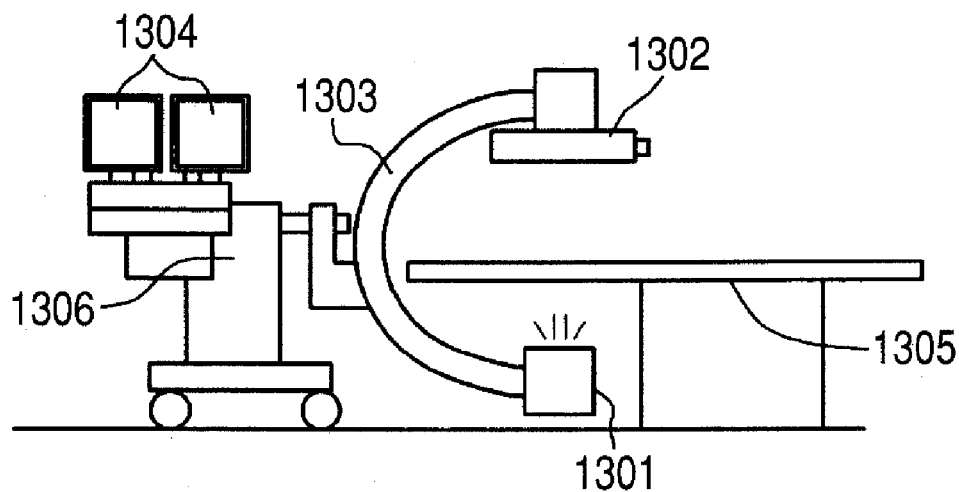

FIGS. 13A and 13B are diagrams illustrating constructional examples of digital radiation (X-ray) imaging systems according to the sixth embodiment of the invention. The digital radiation imaging systems according to the sixth embodiment are fluoroscopic systems as application examples of the radiation imaging apparatuses according to the first to fifth embodiments.

FIG. 13A illustrates the digital radiation imaging system of a C arm (ceiling running type), and FIG. 13B illustrates the digital radiation imaging system of a C arm (mobile type). An X-ray source 1301 corresponds to the radiation generating apparatus 107 in the first to fifth embodiments. A radiation imaging apparatus 1302 corresponds to one of the radiation imaging apparatuses according to the first to fifth embodiments. A C arm 1303 is illustrated. A monitor 1304 displays an image obtained by the radiation imaging apparatus 1302. A bed 1305, a truck (mobile radioscopy system) 1306, and a suspending apparatus 1307 are provided. In FIG. 13B, the X-ray source 1301 and the radiation imaging apparatus 1302 are arranged at two edges of a C-type suspending tool. The C-type suspending tool is fixed to the movable truck 1306.

The term "radioscopy" here denotes motion-image radiographing using X-rays, and the radiographing is continuously executed at a resolution lower than in the case of a still image and at a dosage of the X-ray per image which is smaller than in the still image photographing by one or more digit (order of magnitude). In the radioscopy apparatus, as illustrated in FIGS. 13A and 13B, the radiation imaging apparatus 1302 for obtaining radiation image data (radiation image signal) and the X-ray source (radiation generating apparatus) 1301 are arranged so as to face each other. In the fluoroscopic radiographing, mainly, monitoring can be performed for inserting a catheter or performing a surgical operation. or a diagnosis of a manifestation of a blood vessel or internal organs or the like. A request for a feature of the body to be radiographed from various angles can be satisfied. The radiation imaging apparatus 1302 and the radiation imaging system can perform fluoroscopic radiographing which is used for the medical diagnosis, operations, or the like.

The radiation imaging system shown here can be controlled by, for example, a control PC provided for the truck 1306. The control PC can be transferred to a remote place by a transmitting device such as a telephone line or the like and the doctor can perform the diagnosis at another place by using the control PC. The control PC can function as an image processing unit which can execute various kinds of wellknown image processes. The radiation data can be also stored in a memory of the control PC or a storing device such as a disk-shaped recording medium or the like which is separately provided.

As an X-ray detector of high sensitivity, there is also a system in which a photomultiplier called an image-intensifier (I-I) and a CCD camera are combined. However, in recent years, the high sensitivity and the high operating speed of the radiation imaging apparatus of the flat panel type have progressed, and their performance has improved, to such a level that fluoroscopic radiographing can be sufficiently executed using the latter type of equipment. Therefore, the radioscopy apparatus using the flat panel radiation imaging apparatus can be put into practical use.

According to the flat panel radiation imaging apparatus, since the apparatus itself is smaller in size than that of the I-I or a CCD camera system, there are such excellent features that the radiographing can be performed even at angles which were difficult conventionally, there is no image distortion, and the contrast is high.

As mentioned above, according to the first to sixth embodiments, the radiation imaging apparatus and the radiation imaging system in which good picture quality can be assured by the offset correction while assuring a high frame rate can be provided. Particularly, even in cases where the offset fluctuates, good picture quality, a high frame rate, and promptness (instantaneousness) in displaying can be realized.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-169470, filed Jun. 27, 2008, which is hereby incorporated by reference herein in its entirety.

What is claimed is:

1. A radiation imaging apparatus comprising:
    a sensor array constructed by arranging, in a matrix form, a plurality of pixels each including a converting element configured to convert radiation into charges and a thin film transistor which has a control terminal and two main terminals and in which one of said two main terminals is connected to said converting element in order to output an electric signal according to the charges;
    a driving circuit configured to supply signals to said control terminals of said plurality of thin film transistors on a row-unit basis;
    a reading circuit configured to hold an electric signal read out through the other one of said two main terminals into a first sampling and holding circuit or a second sampling and holding circuit and output an image signal based on the electric signal; and
    a control unit configured to control said driving circuit and said reading circuit,
    wherein, for a period of time until an image signal according to a pulse-shaped radiation is output after termination of irradiation of said sensor array by the pulse-shaped radiation, said control unit
        allows said driving circuit to drive said thin film transistor of a predetermined pixel, thereby allowing a first electric signal to be output from said predetermined pixel,
        allows said driving circuit to drive said thin film transistor of said predetermined pixel in which the first electric signal has been output, thereby allowing a second electric signal to be output from said predetermined pixel, and
        allows said reading circuit to output the image signal based on an electric signal corresponding to a difference between the first electric signal held in the first sampling and holding circuit and the second electric signal held in the second sampling and holding circuit.

2. An apparatus according to claim 1, wherein, after the first electric signal of a predetermined row has been output, before the first electric signal of a row which is driven next to the predetermined row is output, said driving circuit drives said thin film transistor of said predetermined row, thereby allowing the second electric signal to be output.

3. An apparatus according to claim 1, wherein said reading circuit comprises:
    the first sampling and holding circuit configured to hold the first electric signal;
    the second sampling and holding circuit configured to hold the second electric signal; and
    a differential amplifier configured to output the electric signal corresponding to the difference between the first electric signal held in said first sampling and holding circuit and the second electric signal held in said second sampling and holding circuit.

4. An apparatus according to claim 1, wherein each said pixel further includes a transistor for initialization configured to initialize said converting element.

5. An apparatus according to claim 1, wherein each said thin film transistor is provided on an insulating substrate and is made of one of amorphous silicon, polysilicon, and organic material as a main material.

6. An apparatus according to claim 1, wherein, in said thin film transistors among the plurality of pixels, sources are connected to a common signal wiring every column.

7. A radiation imaging system comprising:
    the radiation imaging apparatus according to claim 1; and
    a radiation generating apparatus configured to irradiate said radiation imaging apparatus with the radiation.

8. A control method of a radiation imaging apparatus having
    a sensor array constructed by arranging, in a matrix form, a plurality of pixels each including a converting element configured to convert radiation into charges and a thin film transistor which has a control terminal and two main terminals and in which one of the two main terminals is connected to the converting element in order to output an electric signal according to the charges,
    a driving circuit configured to supply signals to the control terminals of the plurality of thin film transistors on a row-unit basis, and
    a reading circuit configured to hold an electric signal read out through the other one of the two main terminals into a first sampling and holding circuit or a second sampling and holding circuit and output an image signal based on the electric signal,
    wherein for a period of time until an image signal according to a pulse-shaped radiation is output after termination of irradiation of the sensor array with the pulse-shaped radiation, the control method comprises:
    a first outputting step of allowing the driving circuit to drive the thin film transistor of a predetermined pixel, thereby allowing a first electric signal to be output;
    a second outputting step of allowing the driving circuit to drive the thin film transistor of the predetermined pixel in which the first electric signal has been output, thereby allowing a second electric signal to be output; and a third outputting step of allowing the reading circuit to read out the first electric signal and the second electric signal and outputting the image signal based on an electric signal corresponding to a difference between the first electric signal and the second electric signal.

* * * * *